(12) United States Patent
Kuehnel et al.

(10) Patent No.: US 7,942,168 B2
(45) Date of Patent: May 17, 2011

(54) PNEUMATIC AND/OR FLUIDIC MODULE, PNEUMATIC AND/OR FLUIDIC SYSTEM AND METHOD OF MANUFACTURING A PNEUMATIC AND/OR FLUIDIC MODULE

(75) Inventors: Thomas Kuehnel, Boeblingen (DE); Erwin Mueller, Stuttgart (DE); Torsten Briem, Boeblingen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 448 days.

(21) Appl. No.: 12/120,665

(22) Filed: May 15, 2008

(65) Prior Publication Data

US 2008/0283136 A1    Nov. 20, 2008

Related U.S. Application Data

(60) Provisional application No. 60/938,213, filed on May 16, 2007.

(51) Int. Cl.
*F16L 55/00* (2006.01)
(52) U.S. Cl. ......... 138/108; 138/103; 138/157; 138/158
(58) Field of Classification Search .................. 138/108, 138/103, 157, 158; 604/179, 174, 180
See application file for complete search history.

(56) References Cited

U.S. PATENT DOCUMENTS

| | | | | |
|---|---|---|---|---|
| 3,175,262 A | * | 3/1965 | Wilson | 24/16 R |
| 3,324,853 A | * | 6/1967 | Czorny et al. | 604/162 |
| 3,894,706 A | * | 7/1975 | Mizusawa | 248/68.1 |
| 3,942,528 A | * | 3/1976 | Loeser | 604/174 |
| 4,347,998 A | * | 9/1982 | Loree | 248/68.1 |
| 4,479,762 A | | 10/1984 | Bilstad et al. | 417/395 |
| 5,875,821 A | * | 3/1999 | Dumser et al. | 138/162 |
| 6,554,789 B1 | | 4/2003 | Brugger et al. | 604/6.11 |
| 2005/0020959 A1 | | 1/2005 | Brugger et al. | 604/4.01 |

* cited by examiner

*Primary Examiner* — Patrick F Brinson

(57) ABSTRACT

The invention provides a pneumatic and/or fluidic module, a method of producing a pneumatic and/or fluidic module and the use of a pneumatic and/or fluidic module, the pneumatic and/or fluidic module comprising at least one pneumatic and/or fluidic conduit provided to form at least a part of a pneumatic and/or fluidic circuit, said at least one pneumatic and/or fluidic conduit comprising a first part along said conduit and a second part along said conduit, wherein said conduit is provided essentially leak-proof along the interface of the first and the second part by means of the first part comprising a first material at the interface of the first and the second part and by means of the second part comprising a second material at the interface of the first and the second part and wherein the first material is more compressible than the second material.

15 Claims, 2 Drawing Sheets

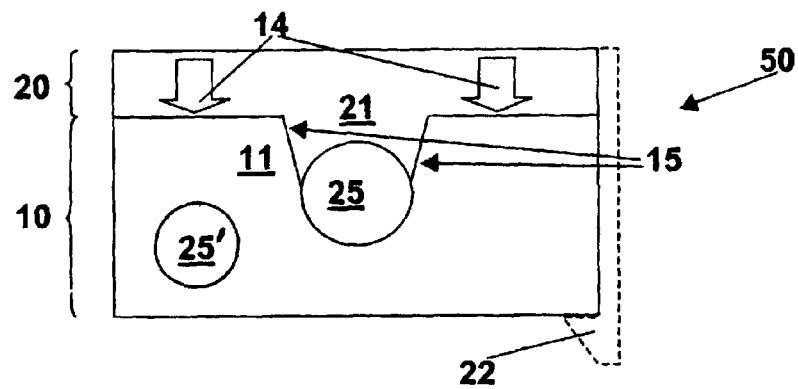
Fig. 1
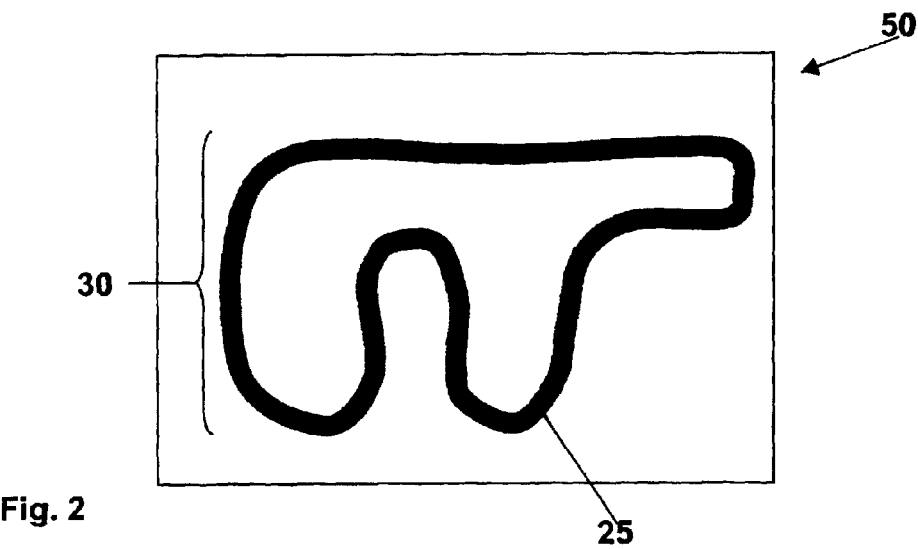
Fig. 2
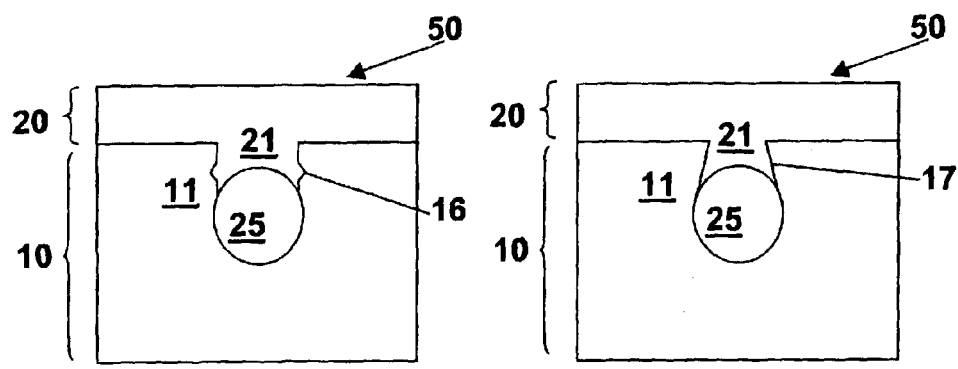
Fig. 3                    Fig. 4

PNEUMATIC AND/OR FLUIDIC MODULE, PNEUMATIC AND/OR FLUIDIC SYSTEM AND METHOD OF MANUFACTURING A PNEUMATIC AND/OR FLUIDIC MODULE

CROSS REFERENCE TO RELATED APPLICATIONS

This application claims the benefit of U.S. provisional application Ser. No. 60/938,213 filed May 16, 2007, which is incorporated herein by reference.

BACKGROUND

The present invention relates to a pneumatic and/or fluidic module, a system and a method of manufacturing a pneumatic and/or fluidic module.

Various methods and apparatuses have been developed which utilise disposable single-use or multiple-use processing systems formed of plastics such as vinyl for accomplishing fluid processing procedures. In the medical field, for example, processing systems have been developed for executing medical tests like the lung capacity by means of spirometers or for executing blood fractionation procedures, wherein the whole blood is separated into one or more fractions by means of either a filter element or by means of centrifugation procedures. Examples of such methods and apparatuses are, e.g., disclosed in U.S. Pat. No. 6,554,789 B1.

These systems generally have the drawback that the known modules are comparably expensive due to the need to carefully assemble the components of which the modules are made. Usually, the known modules either require to use special sealing means like O-ring seals or they need to apply another sealing technique like, e.g., welding, ultrasonic welding or the like. This strongly limits the possibility of cheaply assemble pneumatic and/or fluidic modules, especially by non-trained personnel, resulting in increasing costs, both related to the material and to the manufacturing costs. Furthermore, the special sealing means which are to be inserted between the components of the modules can be omitted during the process of manufacturing, resulting in a reduced tightness or leak-proofness of the modules.

SUMMARY

It is therefore an objective of the present invention to provide a pneumatic and/or fluidic module which can be easily assembled in a very secure manner, resulting in a reduced cost of manufacturing of the pneumatic and/or fluidic module.

The above objective is accomplished by a pneumatic and/or fluidic module, comprising at least one pneumatic and/or fluidic conduit provided to form at least a part of a pneumatic and/or fluidic circuit, said at least one pneumatic and/or fluidic conduit comprising a first part along said conduit and a second part along said conduit, wherein said conduit is provided essentially leak-proof along the interface of the first and the second part by means of the first part comprising a first material at the interface of the first and the second part and by means of the second part comprising a second material at the interface of the first and the second part and wherein the first material is more compressible than the second material.

This has the advantage that a module can be provided where the mains parts of the module are simply plugged together. Due to the characteristics of the first material and the second material being in contact at least in the interface area of the pneumatic and/or fluidic conduit, no additional sealing parts are necessary. Furthermore, it is advantageously possible that no additional bonding or sealing technique is necessary to apply with the module components plugged together. Another advantage is that an increased repeatability of the flow and pressure characteristics is possible to achieve because no intermediate sealing parts are required. Furthermore, reduced manufacturing costs are possible because the inventive module can be assembled very easily. The first part is e.g. provided as a main part of the pneumatic and/or fluidic module. Therefore, the first part is also called the chassis part of the pneumatic and/or fluidic module. The second part is then, for example, provided in the form of a cover or a cap of the pneumatic and/or fluidic module.

According to the invention, it is preferred that the interface of the first and the second part is provided leak-proof by means of an obturating force applied to the interface. Thereby, the sealing capacity of the first material and the second material can be even enhanced. It is preferred that the obturating force obturates the interface between the first part and the second part along the pneumatic and/or fluidic conduit. Thereby, it is possible to provide the pneumatic and/or fluidic circuit more leak-proof or more tight than without an obturating force.

Furthermore, it is preferred according to the present invention, that the obturating force is applied by means of a locking means. Thereby, it is advantageously possible that the inventive module can be assembled by simply lock the locking means to ensure that the pneumatic and/or fluidic circuit inside the pneumatic and/or fluidic module is sufficiently tight.

Very preferably according to the present invention, the locking means is connected with the second part or the locking means is integrally formed with the second part of the pneumatic and/or fluidic module. Thereby, it is advantageously possible not only to plug the first part and the second part of the pneumatic and/or fluidic module together but also to lock the assembly of the first and the second part of the module.

It is furthermore preferred according to the present invention that the locking means is provided as a locking clip. It is thereby possible to provide an easy to use and cheap solution for both plugging and locking the first part together with the second part of the pneumatic and/or fluidic module.

Preferably according to the present invention, the interface of the first and the second part is provided leak-proof by means of form fit shaping the first and second part at the interface. Thereby, it is advantageously possible to provide the function of the obturating force at the interface of the first part and the second part by means of shaping the parts accordingly.

According to the present invention, it is preferred that the form fit shape is provided as a rib at the interface and/or a trapezoidal cross-section of the interface of the first and the second part. Thereby, the form fit shape can be achieved very easily. Furthermore, the assembly of the first part and the second part of the pneumatic and/or fluidic module can be rendered more easy and more error-free because the correct plugging of the first part with the second part can be made detectable, e.g. by means of a sound or a snapping.

Furthermore, it is preferred according to the present invention that the first part comprises a receptacle for a pneumatic component and/or that the first part comprises a receptacle for an electronic circuit board. Thereby, it is advantageously possible to provide the pneumatic and/or fluidic module according to the invention with pneumatic and/or fluidic components and/or an electronic circuit board such that the module provides a functional unit being able to perform, e.g. a test or treatment.

Preferably according to the present invention, the pneumatic and/or fluidic circuit is provided as a multi-layer pneumatic and/or fluidic circuit. It is thereby possible to realise a more complex pneumatic and/or fluidic circuit by means of the first part, the second part and a third part which is plugged preferably to the other side of the first part than the second part is plugged. Of course, further layers are possible to provide, e.g. with a fourth part separated from the first part by the third part or the second part.

The present invention also refers to a method for producing a pneumatic and/or fluidic module, the pneumatic and/or fluidic module comprising at least one pneumatic and/or fluidic conduit provided to form at least a part of a pneumatic and/or fluidic circuit, said at least one pneumatic and/or fluidic conduit comprising a first part along said conduit and a second part along said conduit, the first part comprising a first material at the interface of the first and the second part and the second part comprising a second material at the interface of the first and the second part, and wherein the first material is more compressible than the second material, wherein the method comprises the steps of:

forming the first part and the second part such that the conduit is essentially leak-proof along the interface of the first and the second part only by joining the first material and the second material at the interface of the first and the second part assembling the pneumatic and/or fluidic module by plugging the first part and the second part together. The inventive method has the advantage that it can be performed very easily and rapidly and thereby very cost-effectively.

The present invention further refers to the use of a pneumatic and/or fluidic module for performing a medical test or a medical treatment. This is a preferred application of the present invention because the need for a disposable pneumatic and/or fluidic module is important in the medical sector.

These and other characteristics, features and advantages of the present invention will become apparent from the following detailed description, taken in conjunction with the accompanying drawings, which illustrate, by way of example, the principles of the invention. The description is given for the sake of example only, without limiting the scope of the invention. The reference figures quoted below refer to the attached drawings.

BRIEF DESCRIPTION OF THE DRAWINGS

FIG. 1 illustrates schematically a cross section of a conduit in a pneumatic and/or fluidic module according to the present invention.

FIG. 2 illustrates schematically a top view of the pneumatic and/or fluidic module according to the present invention.

FIGS. 3 and 4 illustrate schematically alternative embodiments of a cross section of a conduit in the pneumatic and/or fluidic module according to the present invention.

DETAILED DESCRIPTION OF THE INVENTION

Figure 5:
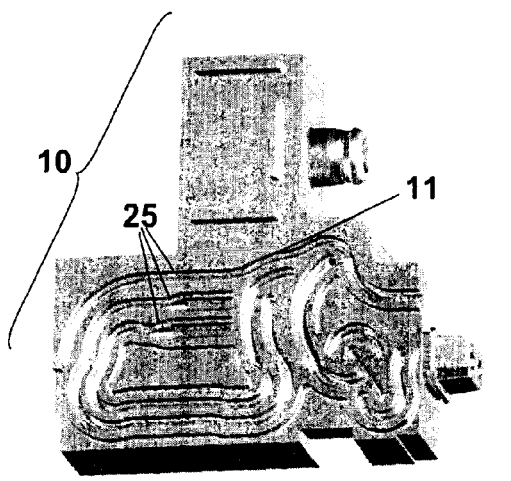
FIGS. 5, 6 and 7 illustrate schematically three-dimensional views of an exemplary embodiment of the pneumatic and/or fluidic module according to the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

Where an indefinite or definite article is used when referring to a singular noun, e.g. "a", "an", "the", this includes a plural of that noun unless something else is specifically stated.

Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described of illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the present description and claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

In FIG. 1, a cross section through a pneumatic and/or fluidic module 50 according to the present invention is schematically shown. It is clear, that normally, a cross section through an inventive pneumatic and/or fluidic module 50 would show a multitude of pneumatic and/or fluidic conduits 25 but for the sake of simplicity, only one pneumatic and/or fluidic conduit 25 is shown in the schematical representation of FIG. 1. The a pneumatic and/or fluidic module 50 comprises at least a first part 10 and a second part 20. Together, these parts 10, 20 realize the pneumatic and/or fluidic conduit 25. This means, that the pneumatic and/or fluidic conduit 25 has a first side adjacent the first part 10 and a second side adjacent the second part 20. At the interface 15 of the first part 10 and the second part 20 along the conduit 25, the two parts 10, 20 have to be sufficiently leak-proof in order to correctly contain the fluid or the gas contained and transported inside the pneumatic and/or fluidic conduit 25. The pneumatic and/or fluidic conduit 25 is represented in figure as having more or less a spherical cross section. Of course, according to the present invention, this is not mandatory. The pneumatic and/or fluidic conduit 25 can also be provided with a cross section of a different form than a spherical or round form. For example, the pneumatic and/or fluidic conduit 25 can be provided with having a rectangular, a trapezoidal, a triangular, a round, an ellipsoidal or another cross section.

According to the present invention, the pneumatic and/or fluidic conduit 25 is located between the first part 10 and the second part 20 (of in recesses of the first part 10 and the second part 20) such that an interface 15 is sufficiently leak-proof for the fluid or the gas or other substance contained by the pneumatic and/or fluidic conduit 25. This can be achieved by applying an obturating force 14 to the interface 15 between the first part 10 and the second part 20 such that the property of being essentially leak-proof is sufficiently maintained along the pneumatic and/or fluidic conduit 25.

According to the present invention, it is possible that the assembly of the first part 10 and the second part 20 is locked by means of a locking means 22, which can be represented by, for example, a locking clip 22. The locking means 22 can either be provided connected to the first part 10 or connected to the second part 20. Alternatively, the locking means 22 can also be provided integrally formed with the first part 10 or the second part 20. Preferably, the locking means is provided by a locking clip 22.

According to the present invention, the interface 15 between the first part 10 and the second part 20 of the inventive pneumatic and/or fluidic module 50 is sufficiently leak-proof along the pneumatic and/or fluidic conduit 25. It is possible according to the present invention, that the surfaces of the first part 10 and the second part 20 which are brought into contact along the interface 15 of the pneumatic and/or the fluidic conduit 15 are provided with a special material for providing a leak-proof contact between the first part 10 and the second part 20. Therefore, the first part 10 comprises a first material 11 and the second part comprises a second material 21. It is possible, that the first part 10 is provided entirely or almost entirely by the first material 11. It is also possible, that the first part 10 is provided with the first material 11 only at the surface contacting the second part 20. Likewise it is possible that the second part 20 is provided entirely or almost entirely by the second material 21. It is furthermore also possible, that the second part 20 is provided with the second material 21 only at its surface being in contact with the first part 10. It is essential according to the present invention, that no further parts, especially sealing materials or sealing compounds are provided in between the first part 10 and the second part 20 in order to provide and essentially leak-proof behaviour of the pneumatic and/or fluidic module 50 along the interface 15 of the pneumatic and/or fluidic conduit 25. This has the great advantage, that no further part or material has to be assembled between the first part 10 or the second part 20. This keeps the production of the pneumatic and/or fluidic module 50 extremely simple and efficient.

In FIG. 2, a top view of the pneumatic and/or fluidic module 50 according to the present invention is presented. It is visible from FIG. 2, that a pneumatic and/or fluidic circuit 30 is provided inside the pneumatic and/or fluidic module 50. The pneumatic and/or fluidic circuit 30 is made of a plurality of pneumatic and/or fluidic conduits 25 which are usually interconnected with one another and/or branched. It is perfectly possible according to the present invention, that the pneumatic and/or fluidic circuit 30 comprises parts which are not adjacent to the first part 10 or to the second part 20. The pneumatic and/or fluidic circuit can be multi-layered such that parts 25' (FIG. 1) of the pneumatic and/or fluidic circuit 30 are located completely inside of the first part 10 and/or completely inside the second part 20. This can be done, by shaping the first part 10 and/or the second part 20 accordingly, e.g. by means of a pressure moulding technique or another shaping technique. Such parts of the pneumatic and/or fluidic circuit 30 which are running completely either inside the first part 10 or inside the second part 20 are normally sufficiently leak-proof, because both the material of the first or the second part 10, 20 is sufficiently leak-proof or tight and the first and/or second part 10, 20 is made by a new one piece of material such that no problem of leakage or tightness inside of the part can occur.

In FIGS. 3 and 4, alternative embodiments of cross sections of a pneumatic and/or fluidic conduit 25 inside the pneumatic and/or fluidic module 50 are shown schematically. Besides the pneumatic and/or fluidic conduit 25, the first part 10 and the second part 20 are represented as well as the interface 15 between the first and the second part 10, 20. At the interface 15, it is shown in FIG. 3 a rib 16 and in FIG. 4 a trapezoidal cross section 17 which provide a form fit shape to the interface 15 between the first part 10 and the second part 20. Thereby, it is possible, that a sufficiently tightness or leak-proofness of the pneumatic and/or fluidic conduit 25 is possible to achieve without applying an obturating force 14 (compare FIG. 1) between the first part 10 and the second part 20. Of course, it is also possible according to the embodiments shown in FIGS. 3 and 4 of the interface 15 to provide an obturating force 14 to the interface 15 in addition to the form fit shape of the interface 15 region.

Figure 6:
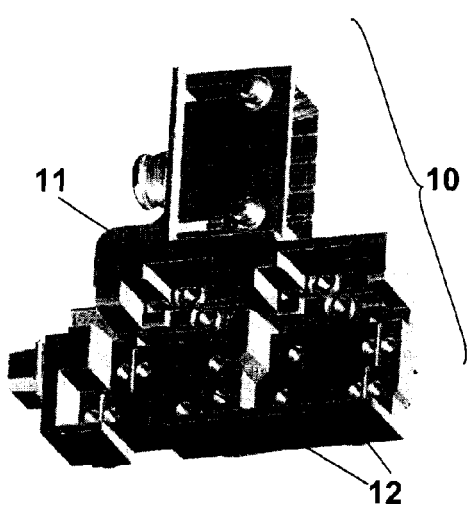
Figure 7:
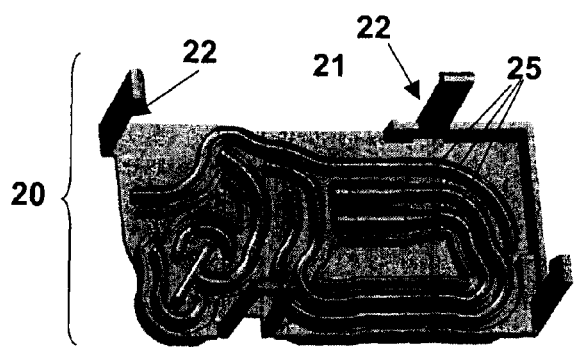

In FIGS. 5, 6 and 7, three-dimensional views of an exemplary embodiment of the pneumatic and/or fluidic module 50 according to the present invention are shown. FIGS. 5 and 6 show in this example the first part 10 and FIG. 7, shows the second part 20. The first part 10 comprises parts of the pneumatic and/or fluidic conduits 25 at one side of the first part 10 (compare FIG. 5). At least this side of the first part 10 is provided with the first material 11. On this side of the first part 10, the second part 20 is plugged or assembled or joined. The second part 20 also comprises part of the pneumatic and/or fluidic conduits 25. Together, the first part 10 and the second part 20 are providing the pneumatic and/or fluidic conduit 25 or conduits 25. The side of the second part 20 comprising partly the pneumatic and/or fluidic conduit 25 is at least partly provided by the second material 21. Furthermore, locking means 22 are provided at the second part 20 for locking assemble the first part 10 and the second part 20. In FIG. 6, a backside of the first part 10 is shown. The backside of the first part 10 comprises receptacles 12 for pneumatic and/or fluidic components (not shown). These pneumatic and/or fluidic components (or alternatively electronic circuit boards) can be connected with the pneumatic and/or fluidic conduit 25 of the other side of the first part 10 by means of recesses or openings 25' in the first part 10. Thereby, the pneumatic and/or fluidic components can be connected to the pneumatic and/or fluidic circuit 30.

According to a preferred aspect of the present invention, the first material 11 is more compressible than the second material 21 or vice versa. This means, that the pneumatic and/or fluidic conduit 25 is provided essentially leak-proof along the interface 15 of the first and the second part 10, 20 by only applying a comparably low obturating force 14 between the first part 10 and the second part 20. Nevertheless, the comparably hard second material 21 is pushed or impressed in the comparably soft first material 11 such that the tightness or leak-proofness of the pneumatic and/or fluidic conduit 25 is achieved.

According to the present invention, it is advantageous, that the pneumatic and/or fluidic module 50 can be produced only by means of assembling the first part 10 with the second part 20. This means, that the first part 10 and the second part 20 are only plugged together without inserting or joining any sealing material in between the first par to and the second part 20. Likewise, no further processing like welding, ultrasonic welding, laser welding or another connecting or sealing technique is necessary to apply in order to provide a sufficient tightness between the first part 10 and the second part 20.

It is preferred that the pneumatic and/or fluidic module 50 is used for medical applications, e.g. for performing medical tests like spirometry tests that assess the capacity of the lung of a patient or other medical tests or treatments, however other applications of the pneumatic and/or fluidic module 50 are also contemplated.

The invention claimed is:

1. A pneumatic and/or fluidic module defining at least a part of a pneumatic and/or fluidic circuit, the module comprising:
   a first part and a second part, the first and second parts engaging to form at least one conduit therebetween, said conduit being essentially leak-proof along an interface between the first and the second parts, the first part comprising a first material at the interface of the first and the second parts and the second part comprising a second material at the interface of the first and the second parts, the first material being more compressible than the second material such that the first and second materials interact to render the interface essentially leak-proof.

2. The pneumatic and/or fluidic module according to claim 1, wherein the first part has a first surface portion that defines at least a lower portion of the conduit and the second part has a second surface portion that defines an upper portion of the conduit.

3. The pneumatic and/or fluidic module according to claim 2, further including:
a locking mechanism which applies an obturating force to the interface.

4. The pneumatic and/or fluidic module according to claim 3, wherein the locking mechanism is one of connected with the second part and integrally formed with the second part.

5. The pneumatic and/or fluidic module according to claim 3, wherein the locking mechanism is provided as a locking clip.

6. The pneumatic and/or fluidic module according to claim 1, wherein at the interface, the first and second parts are shaped to interact in a fluid tight, interfitting relationship.

7. A pneumatic and/or fluidic module comprising at least one pneumatic and/or fluidic conduit provided to form at least a part of a pneumatic and/or fluidic circuit, said at least one pneumatic and/or fluidic conduit comprising a first part along said conduit and a second part along said conduit, wherein said conduit is provided essentially leak-proof along an interface between the first and the second part by:
the first part comprising a first material at the interface between the first and the second parts and the second part comprising a second material at the interface of the first and the second part, the first material being more compressible than the second material; and
a form fit shaping of the first and second parts at the interface, the form fit shape being provided as a rib at the interface and/or a trapezoidal cross-section of the interface of the first and the second parts.

8. The pneumatic and/or fluidic module according to claim 1, wherein the first part defines a receptacle for a pneumatic component.

9. A pneumatic and/or fluidic module comprising:
a pneumatic and/or fluidic circuit including at least one pneumatic and/or fluidic conduit defined by a first part along said conduit and a second part along said conduit, the first and second parts defining an essentially leak-proof interface between the first and the second parts, the first part including a first material at the interface and the second part including a second material at the interface, the first material being more compressible than the second material, the first part defining a receptacle for an electronic circuit board.

10. A pneumatic and/or fluidic module comprising:
a multi-layer pneumatic and/or fluidic circuit, the multi-layer circuit including:
a first part and a second part which taken together define at least one conduit of the fluid circuit, the first part having a first material at an interface between the first and second parts and the second part having a second material at the interface, the first material being more compressible than the second material such that the interface is essentially leak-proof.

11. The pneumatic and/or fluidic module according to claim 2, wherein the first surface portion is softer than the second surface portion.

12. A module comprising:
one or more conduits formed by mating portions of a first part and a second part of the module;
one or more receptacles for mating with a portion of a medical system defined in at least one of the first and second parts; and
an assembly leak-proof interface formed by complementary shape sections of said first and second parts.

13. The module of claim 12, wherein the first part is comprised of a material that is more compressible than a material comprising the second part.

14. The module of claim 13, further comprising a locking mechanism which applies an obturating force.

15. The module of claim 12, wherein the interface is formed by compression of a section of said first part to form the complementary shape to said second part.

* * * * *